United States Patent [19]

Usagawa et al.

[11] Patent Number: 4,977,063
[45] Date of Patent: Dec. 11, 1990

[54] SILVER HALIDE PHOTOGRAPHIC LIGHT-SENSITIVE MATERIAL CAPABLE OF OBTAINING HIGH CONTRAST IMAGES

[75] Inventors: Yasushi Usagawa, Hino; Fumio Ishii, Akishima, both of Japan

[73] Assignee: Konica Corporation, Tokyo, Japan

[21] Appl. No.: 317,719

[22] Filed: Mar. 2, 1989

[30] Foreign Application Priority Data

Mar. 3, 1988 [JP] Japan .................................. 63-50214
Dec. 13, 1988 [JP] Japan ................................ 63-314543

[51] Int. Cl.$^5$ ................................................ G03C 1/34
[52] U.S. Cl. .................................... 430/264; 430/598
[58] Field of Search ................................ 430/264, 598

[56] References Cited

FOREIGN PATENT DOCUMENTS 59-200231 11/1984 Japan .................................. 430/598

Primary Examiner—Paul R. Michl
Assistant Examiner—Janet C. Baxter
Attorney, Agent, or Firm—Finnegan, Henderson, Farabow, Garrett, and Dunner

[57] ABSTRACT

A silver halide photographic light-sensitive material is disclosed, which is inhibited in formation of pepper spot in a halftone image and capable of making extremely high contrast image thereon. The light-sensitive material contains a compound represented by the following formula:

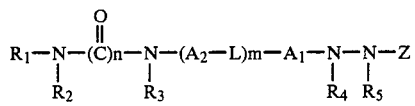

wherein $A_1$ and $A_2$ are each an arylene group or a divalent heterocyclic group; L is a linking group; z is a formyl group, an acyl group, a sulfonyl group, a carbamoyl group, a sulfamoyl group, an alkoxycarbonyl group, a thioacyl group or a

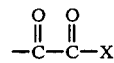

group; X is $-NR_6R_7$ or $-OR_8$, in which $R_6$ and $R_7$ are each a hydrogen atom, an alkyl group, an alkenyl group, an alkynyl group, a heterocyclic group, a hydroxy group, an alkoxy group, an alkenylkoxy group, an alkynyloxy group, an aryloxy group, or a heterocyclic oxy group, and $R_8$ is a hydrogen atom, an alkyl group, an alkenyl group, an alkynyl group, an aryl group or a heterocyclic group; n is 1 or 2; m is 0 or 1; $R_1$ and $R_2$ are each a hydrogen atom, an alkyl group, an alkenyl group, an alkynyl group, an aryl group, a heterocyclic group or an amino group, provided that when n is 1, at least one of the $R_1$ and $R_2$ is an amino group; $R_3$ is a hydrogen atom or an alkyl group; and $R_4$ and $R_5$ are each a hydrogen atom or a substituent.

15 Claims, No Drawings

SILVER HALIDE PHOTOGRAPHIC LIGHT-SENSITIVE MATERIAL CAPABLE OF OBTAINING HIGH CONTRAST IMAGES

FIELD OF THE INVENTION

This invention relates to a silver halide photographic light-sensitive material and particularly to a silver halide photographic light-sensitive material capable of obtaining high contrast images.

BACKGROUND OF THE INVENTION

Heretofore, silver halide photographic light-sensitive materials have widely been applied to graphic arts processes. The above-mentioned graphic arts process comprises a step where an original's image having continuous tone is converted into a half-tone dot image, i.e., a step where the density variations in the original's continuous tone are converted into the congregation of half-tone dots each having an area proportionate to the above-mentioned density variations.

Heretofore, a half-tone dot image has been formed of an original in such a manner that the original has been photographed through a cross-line screen or a contact screen on a silver halide photographic light-sensitive material having hard-contrast photographic characteristics and the photographed light-sensitive material has then been developed.

For the purpose of providing an image with a hard-contrast characteristic, a silver halide photographic light-sensitive material has been contained with a compound such as hydrazine serving as the so-called contrast-increasing agent as disclosed in, for example, Japanese Patent Publication Open to Public Inspection (hereinafter referred to as Japanese Patent O.P.I. Publication) No. 56-106244/1981 and U.S. Pat. No. 4,686,167, further, the light-sensitive material has been added with silver halide grains capable of effectively promoting the contrast-increasing characteristics of the compound, or, a suitable combination of other photographic additives has been used, so that a desirable photographic light-sensitive material has been prepared. Such silver halide photographic light-sensitive material thus prepared has been certainly capable of serving as a stable light-sensitive material and obtaining a high contrast photographic image even if it is treated with a rapidly processable developing solution.

However, such silver halide photographic light-sensitive materials as those mentioned above have had the problem that sand-grain shaped or pin-point shaped fog, that is so-called black spot fog or pepper spot, when a continuous tone original has been converted into a half-tone dot image, so that the quality of the half-tone dot image has been damaged. For the purpose of solving this problems, therefore, there have often taken the measures of adding various types of stabilizers or inhibitors each having a hetero atom, or the like measures. These measures cannot always be effective to satisfy the purpose.

SUMMARY OF THE INVENTION

This invention was made for solving the above-mentioned problem. It is, therefore, an object of the invention to provide a silver halide photographic light-sensitive material provided with hard-contrast photographic characteristics and also inhibited a half-tone dot image from being fogged.

The object of the invention can be achieved with a silver halide photographic light-sensitive material comprising at least one silver halide emulsion layer wherein a compound represented by the following formula I is contained:

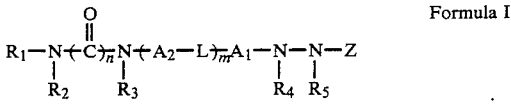

Formula I wherein $A_1$ and $A_2$ are each an arylene group or a heterocyclic group; L is a bonding group: Z is a formyl group, an acyl group, a sulfonyl group, a carbamoyl group, a sulfamoyl group, an alkoxycarbonyl group, a thioacyl group or a

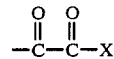

group: X is $-NR_6R_7$ or $-OR_8$, in which $R_6$ and $R_7$ are each a hydrogen atom, an alkyl group, an alkenyl group, an alkynyl group, an aryl group, a heterocyclic group, a hydroxy group, an alkoxy group, an alkenyloxy group, an alkynyloxy group, an aryloxy group or a heterocyclic oxy group, the groups represented by $R_6$ and $R_7$ may be bond together to form a ring, and $R_8$ is a hydrogen atom, an alkyl group, an alkenyl group, an alkynyl group, an aryl group or a heterocyclic group; n is 1 or 2; m is 0 or 1; $R_1$ and $R_2$ are each a hydrogen atom, an alkyl group, an alkenyl group, an alkynyl group, an aryl group, a heterocyclic group or an amino group: $R_3$ is a hydrogen atom or an alkyl group; each pair of $R_1$ and $R_2$, and $R_1$ and $R_3$ may be bond to form a ring provided that when n is 1, at least one of $R_1$ and $R_2$ is an amino group: and $R_4$ and $R_5$ are each a hydrogen atom or a substituent.

DETAILED DESCRIPTION OF THE INVENTION

Formula I will be detailed below.

$A_1$ and $A_2$ represent each an arylene group such as a group of phenylene, naphthylene or the like, or a heterocyclic group such as a group of thiophen-di-yl, furan-di-yl, pyridine-di-yl or the like; L represents a bonding group such as a group of $-SO_2NH-$, $-CONH-$, $-O-$, $-OCH_2CONH-$, $-CH=N-$ or the like: Z represents a formyl group, an acyl group such as a group of acetyl, trifluoroacetyl, α-(2,4-di-t-amylphenoxy)acetyl, methoxyacetyl, cyanoacetyl, benzoyl or the like, a sulfonyl group such as a group of methylsulfonyl, toluenesulfonyl, 4-dodecyloxybenzenesulfonyl or the like, a carbamoyl group such as a group of carbamoyl, dodecylcarbamoyl, dimethylcarbamoyl or the like, a sulfamoyl group such as a group of sulfamoyl, butylsulfamoyl, dimethylsulfamoyl or the like, an alkoxycarbonyl group such as a group of methoxycarbonyl, tetradecyloxycarbonyl or the like, a thioacyl group such as a group of thioformyl, thioacetyl or the like, a group represented by

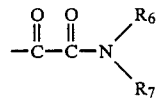

or a group

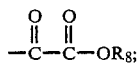

$R_6$ and $R_7$ represent each a hydrogen atom, an alkyl group such as a group of methyl, ethyl, methoxyethyl, cyanoethyl, hydroxyethyl, 4-(2,4-di-t-amylphenoxy)butyl, benzyl, trifluoroethyl or the like, an alkenyl group such as a group of allyl, butenyl, pentenyl, pentadienyl or the like, an alkynyl group such as a group of propargyl, butynyl, pentynyl or the like, an aryl group such as a group of phenyl, naphthyl, cyanophenyl, methoxyphenyl or the like, a heterocyclic group including, for example, an unsaturated heterocyclic group such as a group of pyridine, thiophene, furan or the like or a saturated heterocyclic group such as a group of tetrahydrofuran, sulforan or the like, a hydroxy group, an alkoxy group such as a group of methoxy, ethoxy, benzyloxy, cyanomethoxy or the like, an alkenyloxy group such as a group of allyloxy, butenyloxy or the like, an alkynyloxy group such as a group of propargyloxy, butynyloxy or the like, an aryloxy group such as a group of phenoxy, naphthyloxy or the like, a heterocyclic-oxy group such as a group of pyridyloxy, pyrimidyloxy or the like, provided that $R_6$ and $R_7$ are allowed to form, together with a nitrogen atom, a ring such as that of piperidine, piperazine, morpholine or the like.

The alkyl, alkenyl, alkynyl, aryl and hetericyclic groups each represented by $R_8$ include, typically, the same groups as those given for the foregoing $R_6$ and $R_7$.

The alkyl, alkenyl, alkynyl, aryl and hetericyclic groups each represented by $R_1$ or $R_2$ include, typically, the same groups as those given for the foregoing $R_6$ and $R_7$. The amino groups represented by $R_1$ or $R_2$ include, for example, a group of α-(2,4-di-t-amylphenoxy)-butylamino, ureido, thioureido, anilino, alkylamino or the like.

The amino groups represented by $R_1$ or $R_2$ further include a group represented by

wherein $R_9$ and $R_{10}$ each represent an alkyl, alkenyl, alkynyl, aryl or heterocyclic group, provided that $R_9$ and $R_{10}$ are allowed to form together a ring.

The groups represented each by $R_9$ or $R_{10}$ include typically the same groups as those given for the foregoing $R_6$ and $R_7$.

$R_3$ represents a hydrogen atom, an alkyl group such as a group of methyl, ethyl, benzyl or the like, $R_1$ and $R_2$ or $R_1$ and $R_3$ are also allowed to form a heterocyclic ring such as a morpholine ring.

The aryl or heterocyclic groups each represented by $A_1$ or $A_2$ include ones introduced thereinto with various substituents including, for example, a halogen atom and a group of alkyl, aryl, alkoxy, aryloxy, acyloxy, alkylthio, arylthio, sulfonyl, alkoxycarbonyl, aryloxycarbonyl, carbamoyl, sulfamoyl, acyl, amino, alkylamino, arylamino, acylamino, sulfonamido, arylaminothiocarbonylamino, hydroxy, carboxy, sulfo, nitro, cyano and so forth.

It is preferred that the compounds represented each by the foregoing Formula I contain at least one anti-diffusion group or a silver halide adsorption acceleration group. Such anti-diffusion groups preferably include a ballast group popularly used in an immobile photographic additive such as couplers and so forth. Such ballast group is a group having 8 or more carbon atoms and being photographically relatively inert. These ballst groups may be selected from a group consisting of an alkyl group, an alkoxy group, a phenyl group, an alkylphenyl group, a phenoxy group, an alkylphenoxy group and so forth.

The silver halide adsorption acceleration groups include, for example, those described in U.S. Pat. No. 4,385,108 such as a thiourea group, a thiourethane group, a heterocyclic thioamido group, a mercapto heterocyclic group, a triazole group and so forth.

$R_4$ and $R_5$ are each hydrogen atom or a substituent including, for example, a sulfonyl group such as a group of methanesulfonyl, toluenesulfonyl or the like, an acyl group such as a group of acetyl, trifluoroacetyl, ethoxycarbonyl or the like, an oxalyl group such as a group of ethoxalyl, pyruvoyl or the like. The compounds represented each by the foregoing Formula I further include those given above.

The compounds preferably used in the invention include those each in which n denoted in the foregoing Formula I is an integer of 1 and the $R_1$ or $R_2$ denoted therein represents an amino group having the aforegiven formula

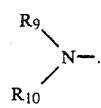

The compounds preferably used in the invention include those each in which Z denoted in Formula I represents a group of formyl group, an acyl group or

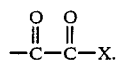

The typical compounds represented by the foregoing Formula I include the following ones. It is, however, to be understood, as a matter of course, that the compounds which are applicable to the invention and concretely represented by Formula I shall not be limited to the compound given below.

Concrete examples of compounds

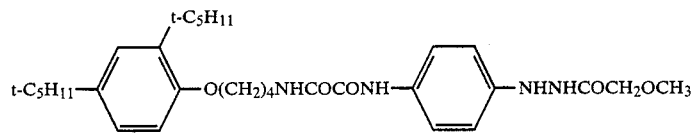

(1)

-continued
Concrete examples of compounds
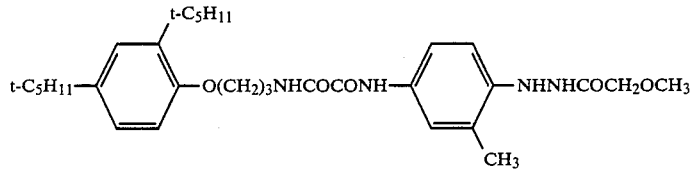  (2)
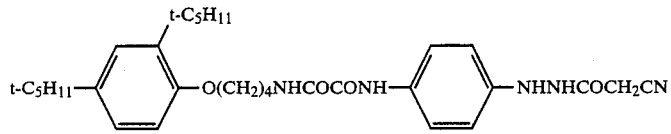  (3)
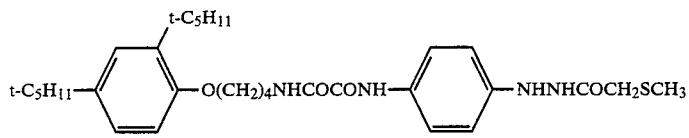  (4)
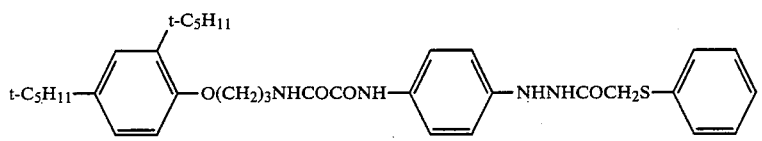  (5)
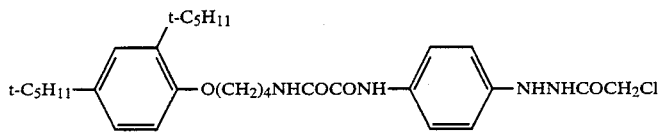  (6)
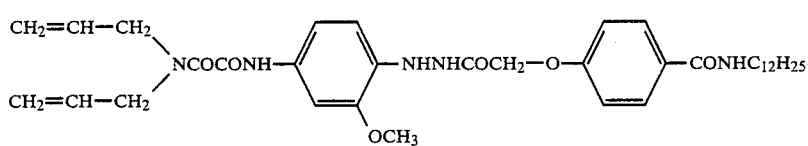  (7)
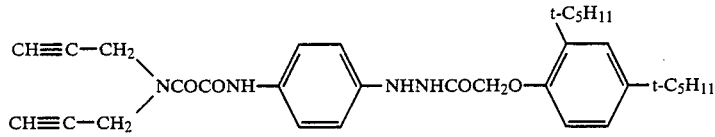  (8)
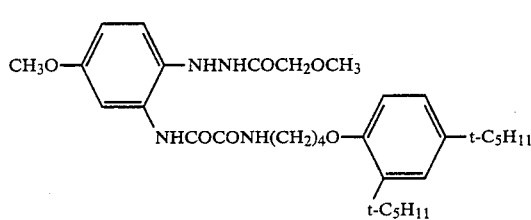  (9)
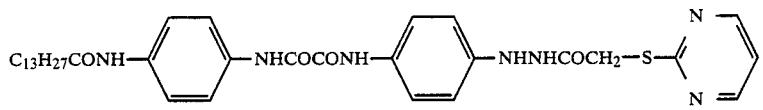  (10)
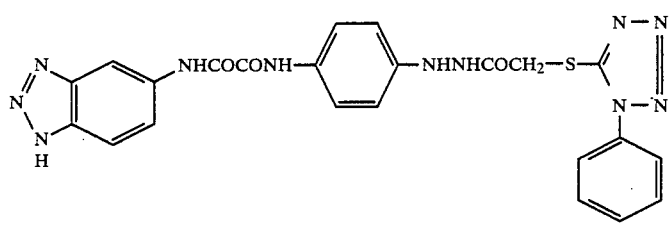  (11)

-continued
Concrete examples of compounds
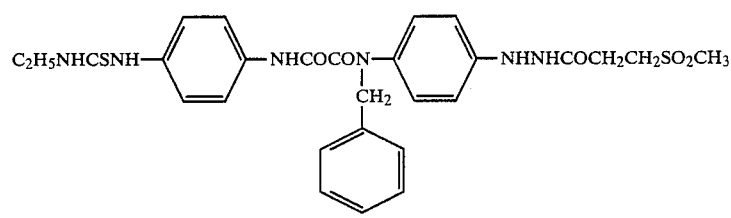 (12)
 (13)
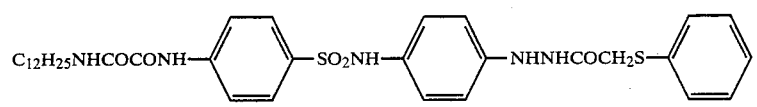 (14)
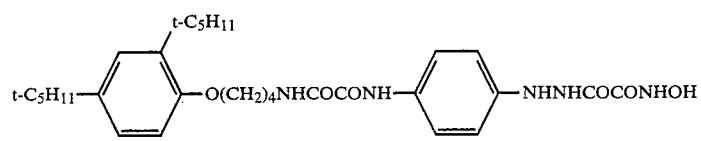 (15)
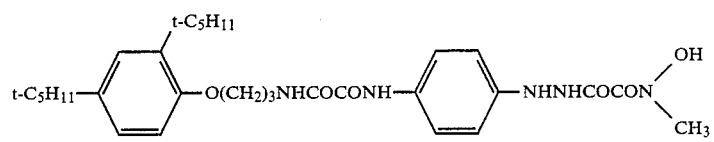 (16)
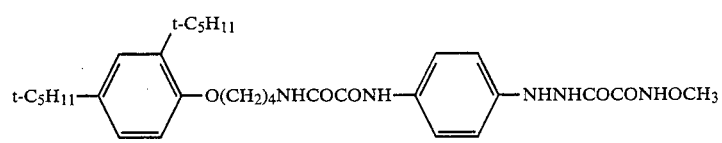 (17)
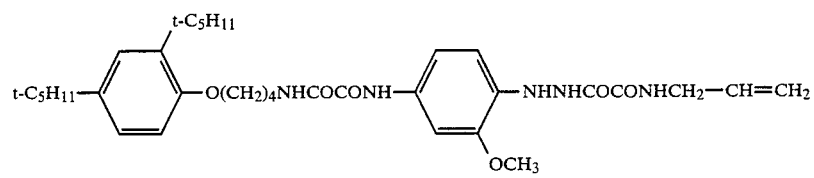 (18)
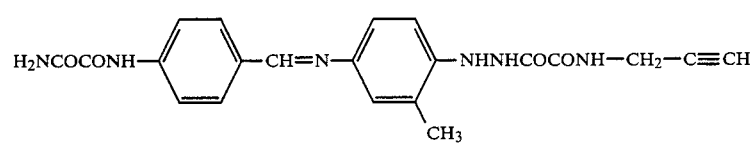 (19)
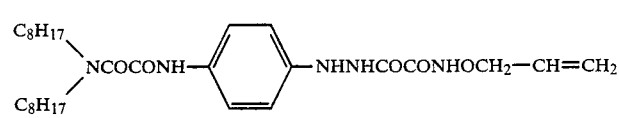 (20)
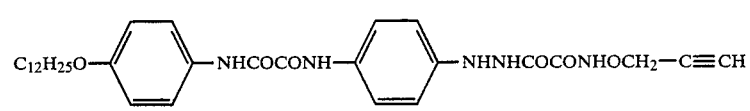 (21)
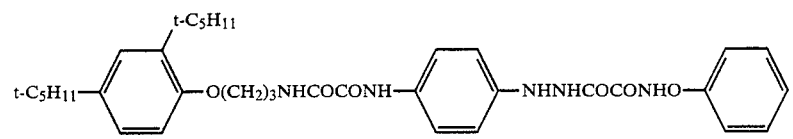 (22)

-continued
Concrete examples of compounds
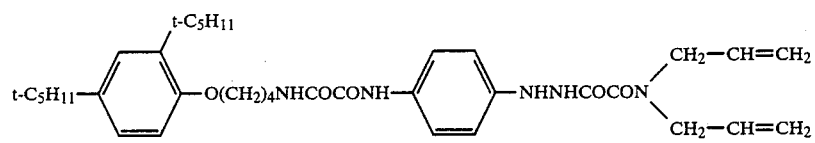 (23)
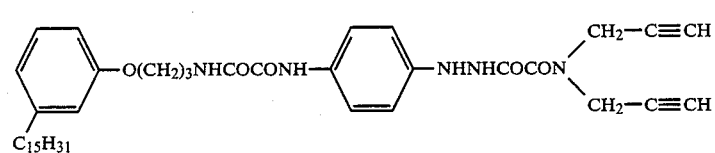 (24)
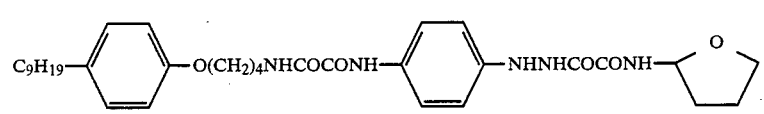 (25)
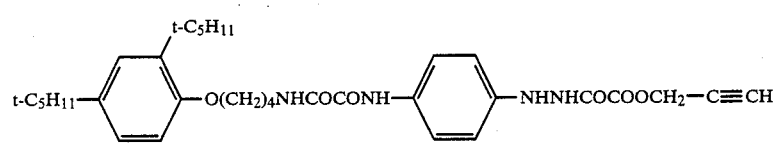 (26)
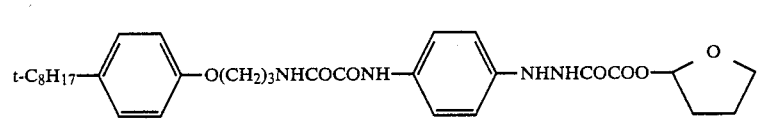 (27)
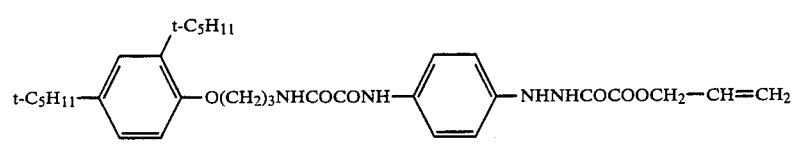 (28)
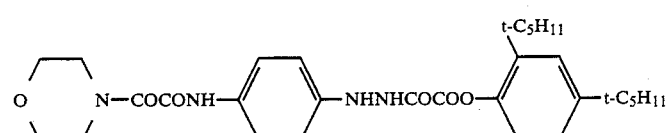 (29)
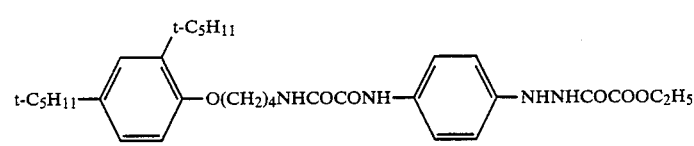 (30)
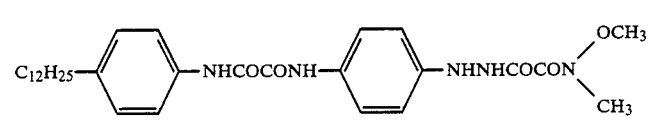 (31)
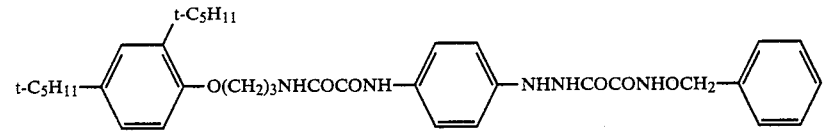 (32)
 (33)

-continued
Concrete examples of compounds
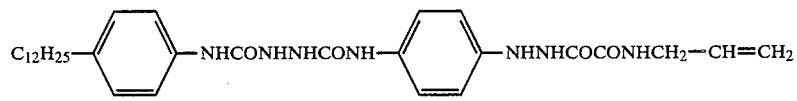 (34)
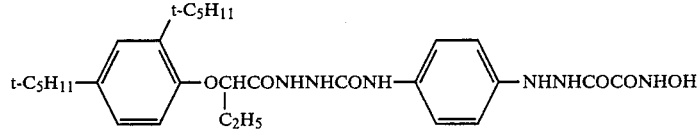 (35)
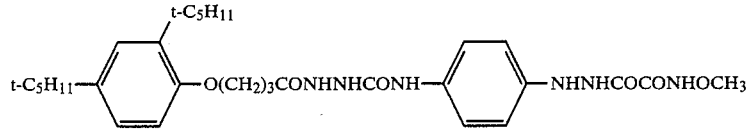 (36)
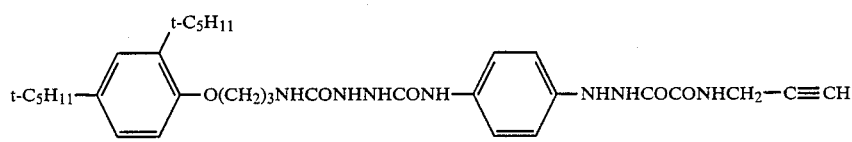 (37)
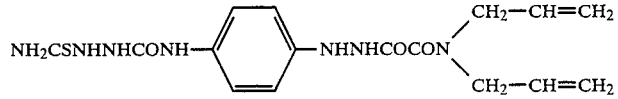 (38)
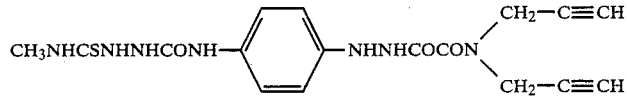 (39)
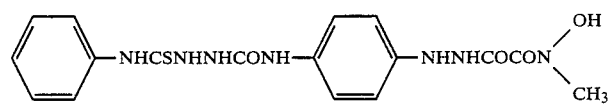 (40)
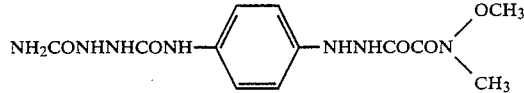 (41)
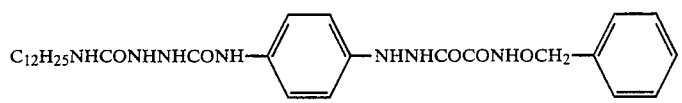 (42)
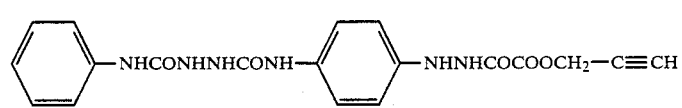 (43)
 (44)
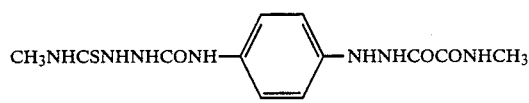 (45)

-continued
Concrete examples of compounds
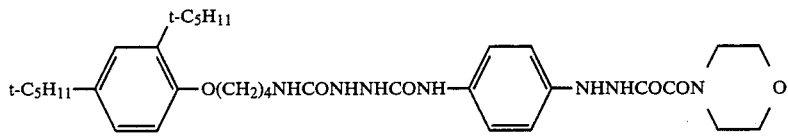  (46)
  (47)
  (48)
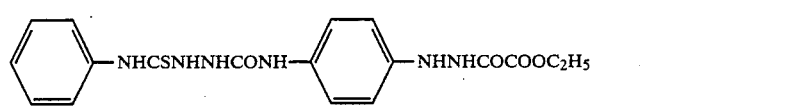  (49)
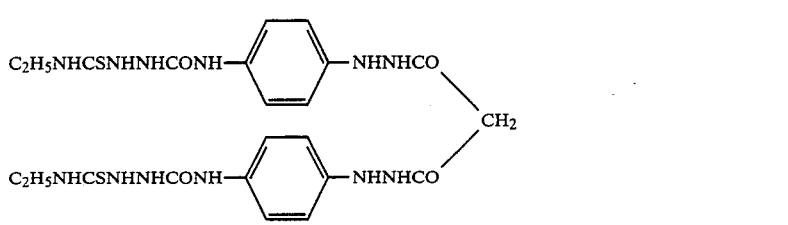  (50)
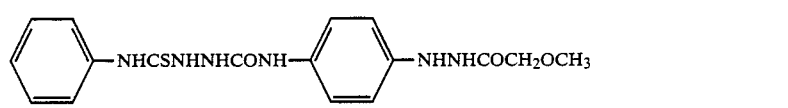  (51)
  (52)
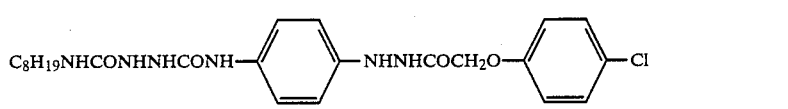  (53)
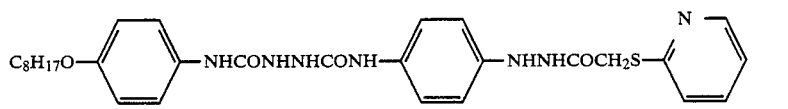  (54)
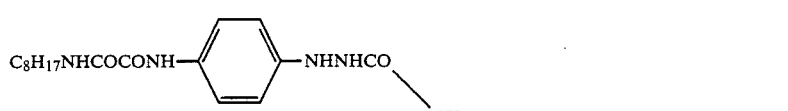  (55)
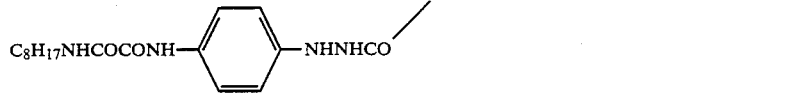  (56)
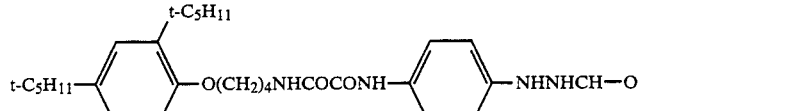

-continued
Concrete examples of compounds
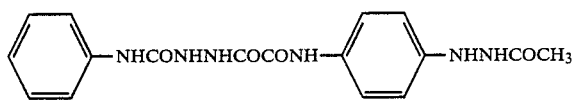 (57)
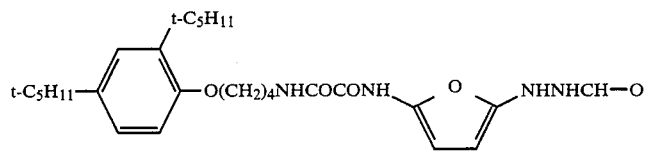 (58)
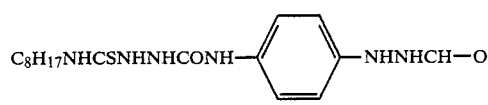 (59)
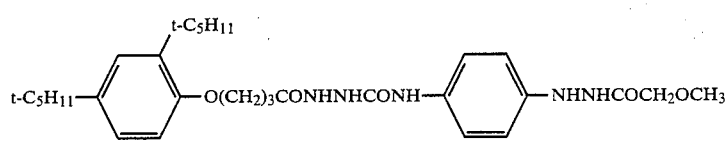 (60)
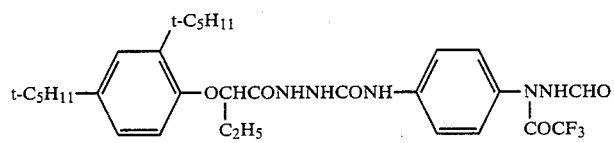 (61)
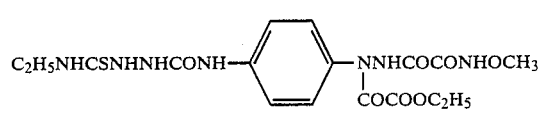 (62)
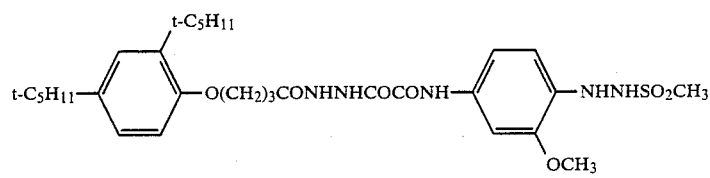 (63)
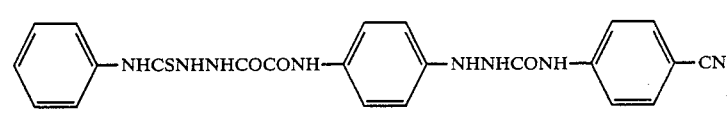 (64)
 (65)
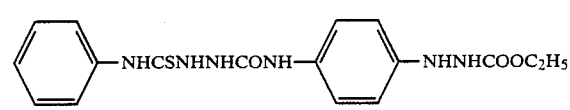 (66)
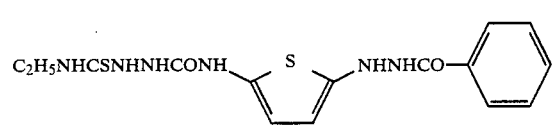 (67)

-continued
Concrete examples of compounds
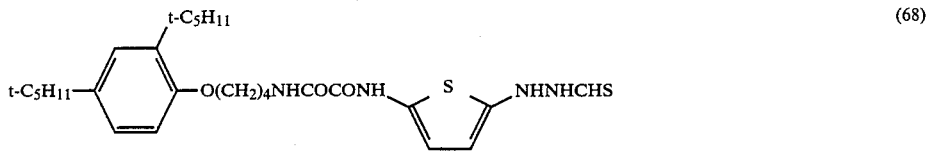
(68)
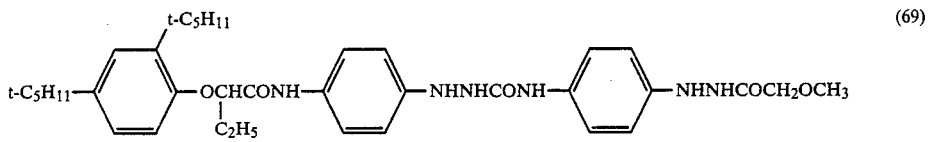
(69)
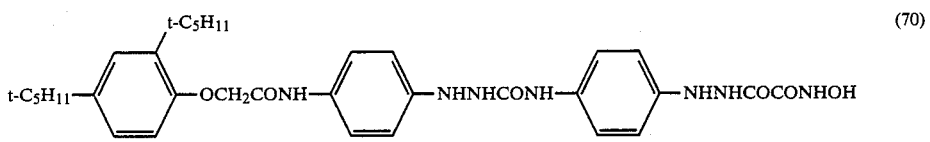
(70)
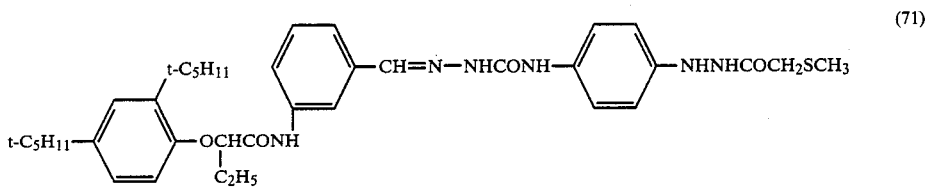
(71)
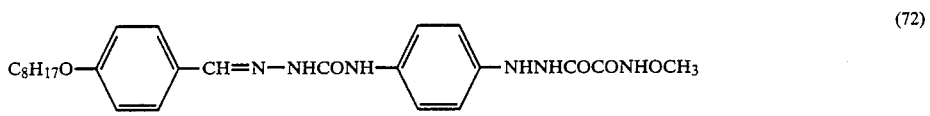
(72)
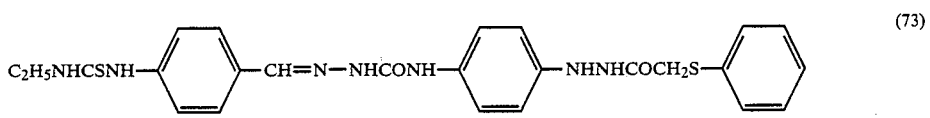
(73)
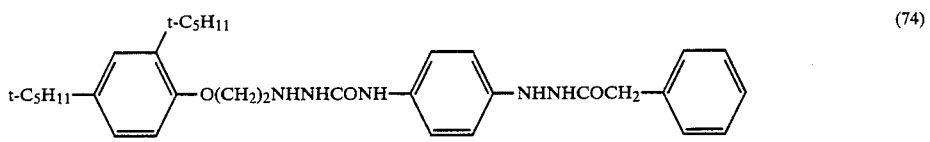
(74)
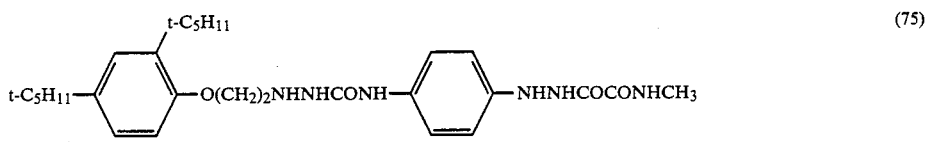
(75)
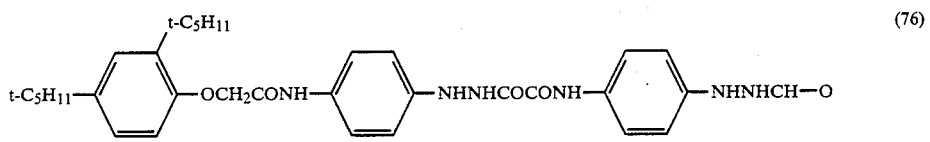
(76)
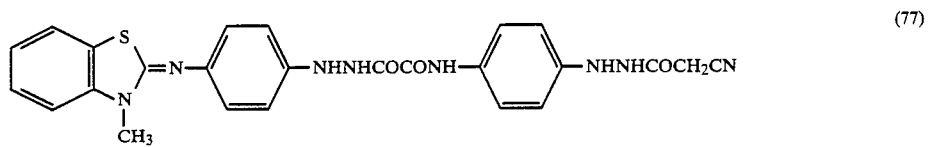
(77)
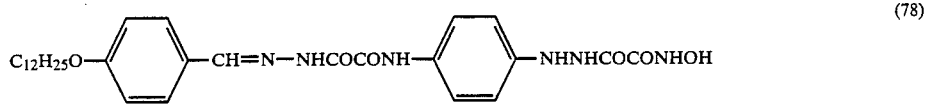
(78)

-continued
Concrete examples of compounds
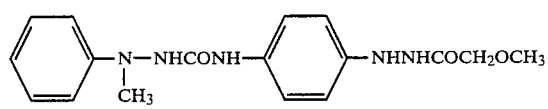 (79)
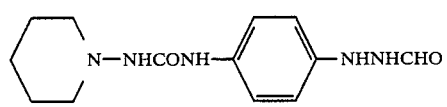 (80)
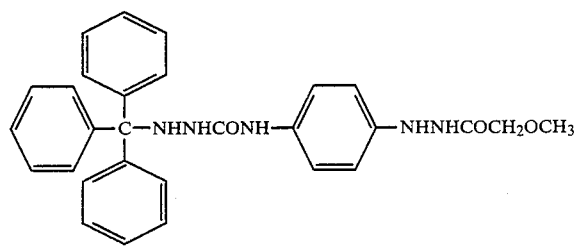 (81)
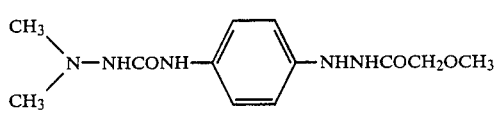 (82)
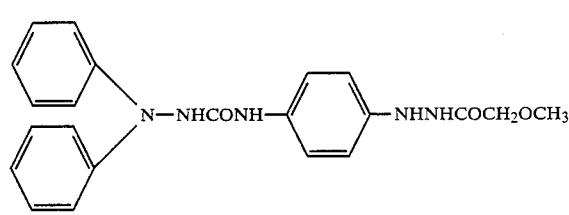 (83)
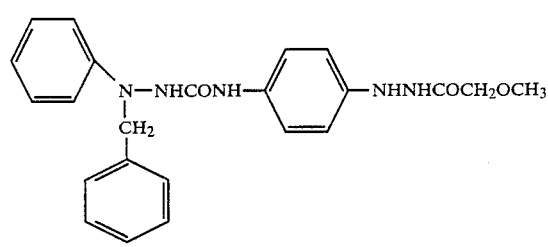 (84)
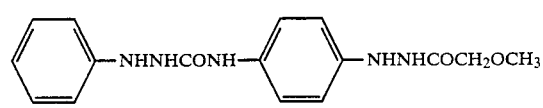 (85)
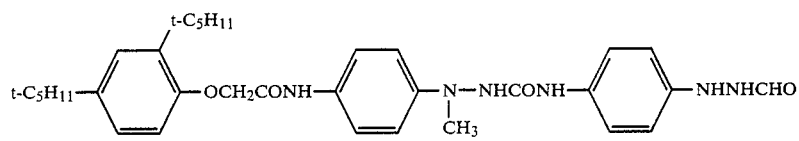 (86)
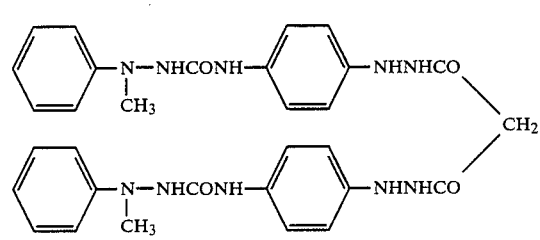 (87)

-continued
Concrete examples of compounds
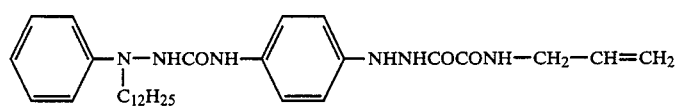 (88)
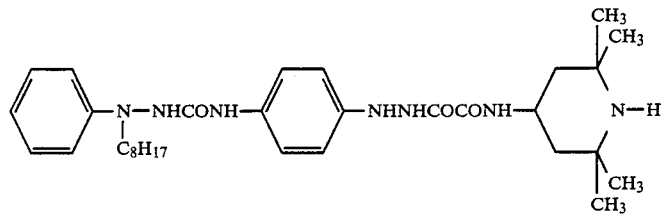 (89)
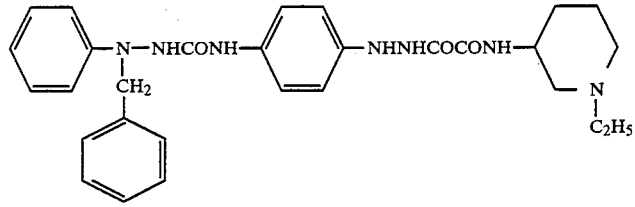 (90)
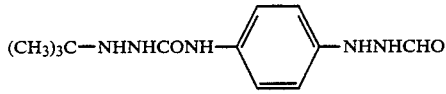 (91)
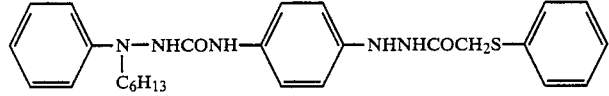 (92)
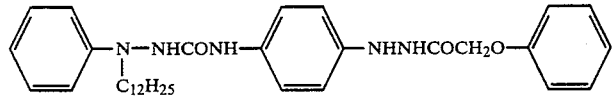 (93)
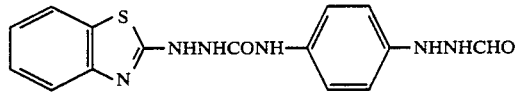 (94)
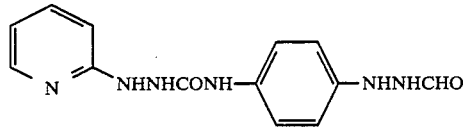 (95)
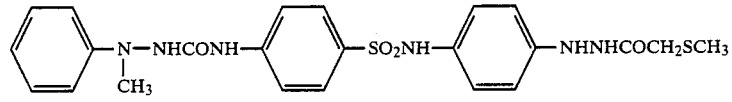 (96)
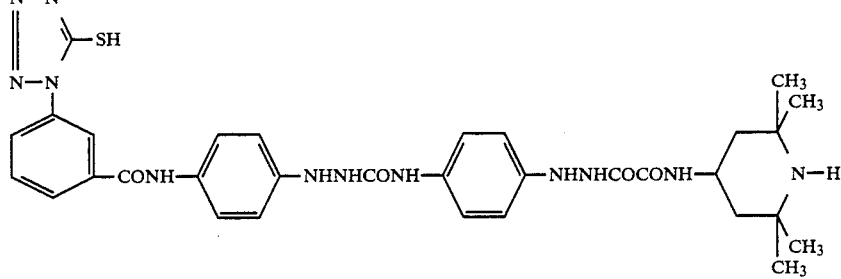 (97)

-continued
Concrete examples of compounds
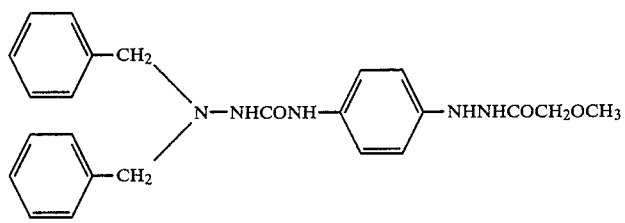
(98)
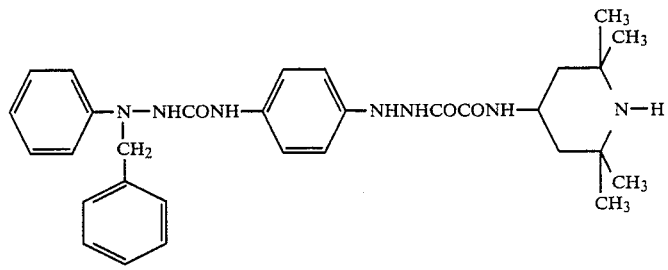
(99)
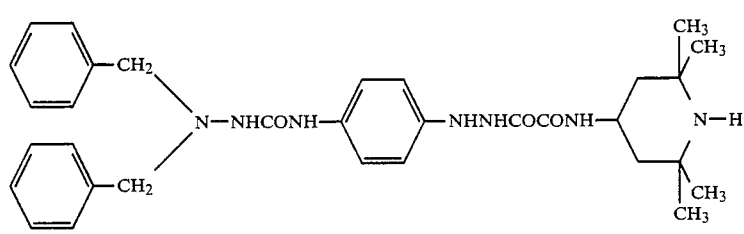
(100)
Next, how to synthesize the compounds relating to the invention represented by Formula I will be described, as examples.
The above-given exemplified compounds 1 can be synthesized in the following method, for example.
Compound (1)
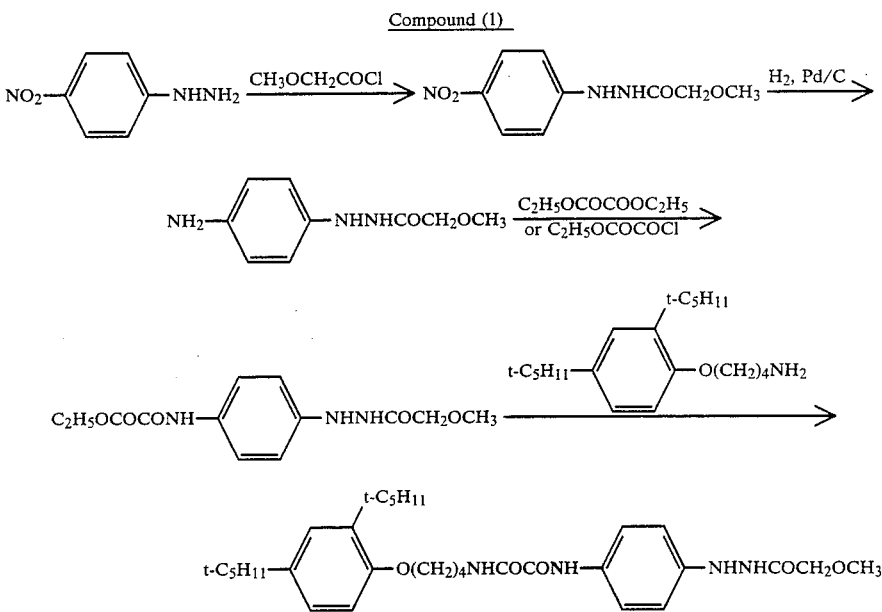
Exemplified compound 17 can be synthesized in the following method.

Compound (17)
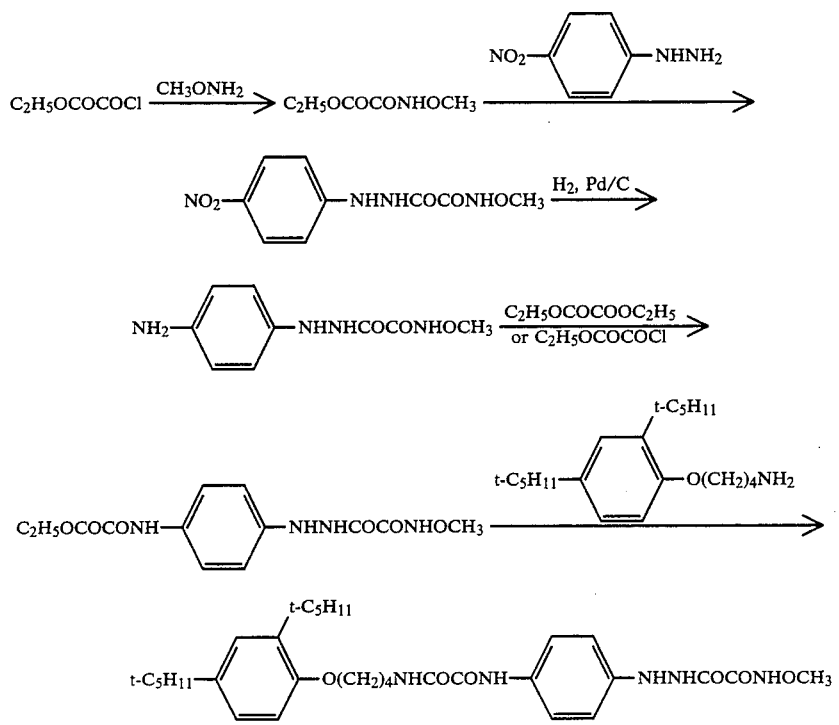
Exemplified compound 52 can be synthesized in the following method.
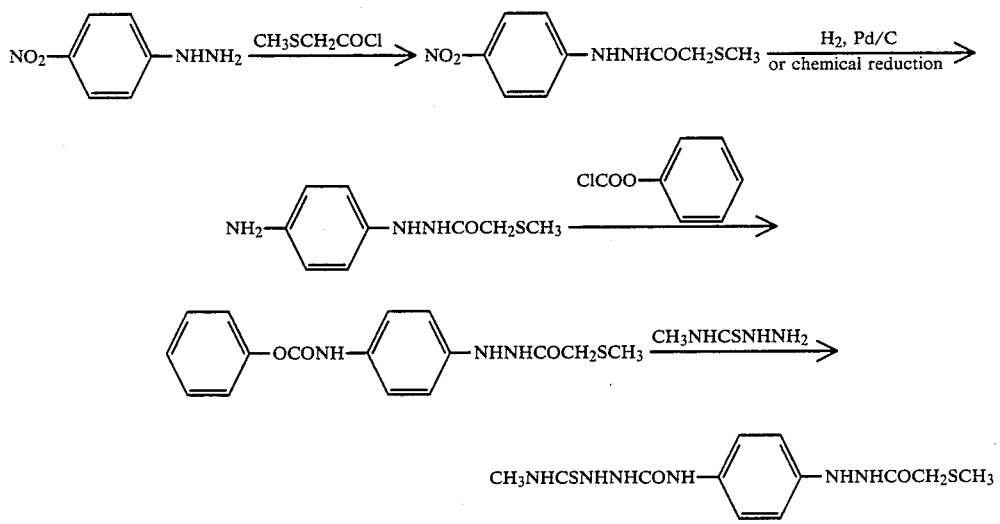
Exemplified compound 60 can be synthesized in the following method.
Compound (60)
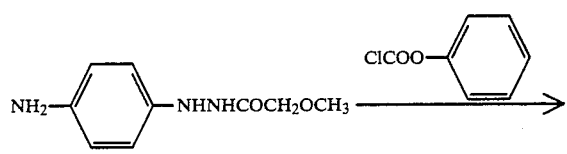

-continued
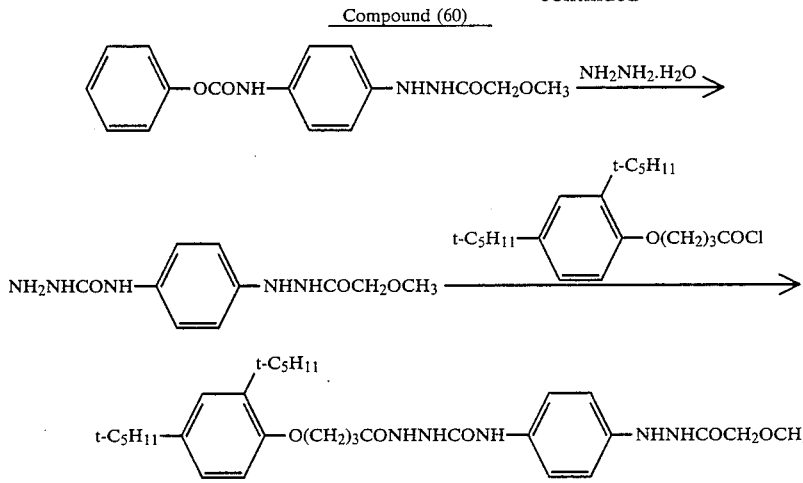
Exemplified compound 69 can be synthesized in the following method.
The synthesis scheme is as follows.
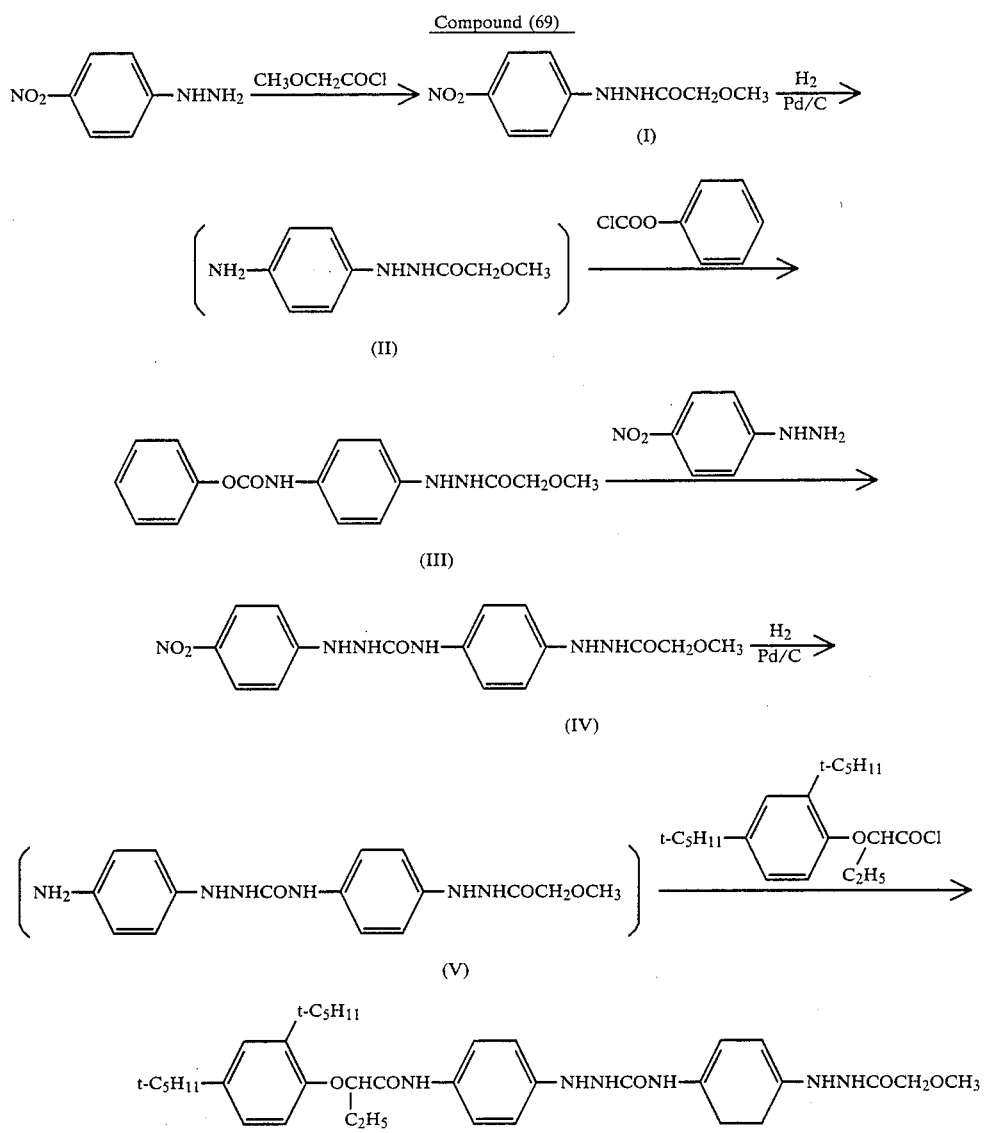

p-nitrophenyl hydrazine of 325 grams are added into 1700 ml of acetonitrile. Triethylamine of 279 g are dropped into the resulted mixture with strongly stirring at a temperature of not higher than 10° C. and 278 g of methoxyacetyl chloride are then added thereinto at the same temperature.

After one hour, 28 g of methoxyacetyl chloride are further added and are then reacted together for 20 minutes. The resulting reaction solution is poured into 2.6 liters of water and is then adjusted to be pH 4.5 to 5.0 with a 30% NaOH solution. The resulting solution is condensed to be about one half and is then crystallized with cooling overnight. The deposited crystals are filtrated and, after they are dried, the resulting crude matters are column-refined with an ethyl acetate/n-hexane (3/1) solution, so that 175 g of compound I can be obtained.

Then, an acetic acid solution containing 9.1 g of Compound VI is dropped at room temperature. After a reaction is carried out at room temperature for 5 hours, the resulting reaction solution is condensed and, after the condensation is neutralized with a 30% NaOH solution, the remaining water is removed in decantation and the residues are dissolved with ethyl acetate and then the solution is condensed after dehydration. The resulting matter is chromatographically refined with a chloroform/methanol mixture having a proportion of 10:1 and recrystallized with an ethyl acetate/n-hexane mixture, so that 6.3 g of Compound 69 can be obtained, Melting point: 125° to 126° C.

M+ = 646 was detected with FAB-MS.

Exemplified compound 79 can be synthesized in the following method.

The synthesis scheme is as follows.

Compound (79)

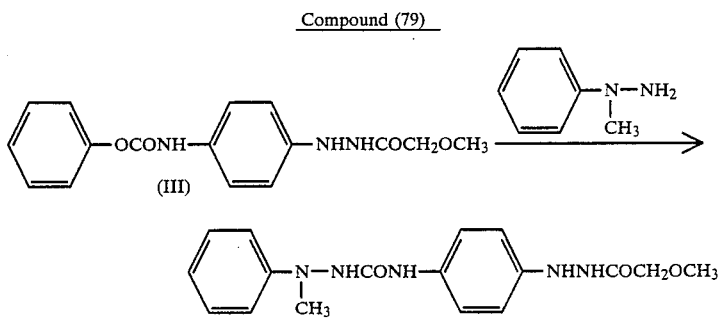

Compound I of 173 g and a 5% Pd/C catalyst of 35 g are added into 1200 ml of acetic acid and a reduction-reaction of the resulting matter is carried out with blowing hydrogen-gas at room temperature and at an ordinary pressure.

After the reaction is completed, the catalyst is removed and 64.5 g of sodium acetate are added into the resulting filtrated solution containing Compound II. Then, 120 g of phenyl chloroformate are dropped at a temperature of not higher than 15° C. and a reaction is carried out for 3 hours.

After the reaCtion is completed, the resulting reacted solution is condensed and the condensation is poured into 1200 ml of water. The mixed solution is adjusted to be pH 6.5, while cooling with water, by making use of a 30% NaOH solution. The deposited crystals are filtrated and the resulting crystals are washed with 500 ml of water and then with 1700 ml of an isopropanol solution with stirring for one hour. After filtrating it, the resulted fitrate is washed with 300 ml of isopropylether and dried, so that 153 g of Compound III can be obtained.

Compound III of 16 g and p-nitrophenyl hydrazine of 11.5 g are added into 200 ml of pyridine and the resulting matter is reacted at 100° C. for 8 hours.

After the reaction is completed, the resulting reacted solution is condensed to obtain crystals. The resulting crystals are washed with methanol and dried, so that 10.5 g of Compound IV can be obtained.

Compound IV of 10 g and a 5% Pd/C catalyst of 4 g are added into 700 ml of acetic acid and a reduction-reaction of the resulting matter is carried out with blowing hydrogen-gas at room temperature and at an ordinary pressure.

After the reaction is completed, the catalyst is removed and 2.4 g of sodium acetate are added into the resulting filtrated solution containing Compound V.

After 25 g of Compound III and 11.6 g of 1-methyl-1-phenylhydrazine are added into 250 ml of pyridine, the resulting mixture is reacted at 100° C. for 8 hours and 3 g of 1-methyl-1-phenylhydrazine are further added thereto. The resulting matter is reacted overnight. After completing the reaction, the resulting reaction solution is condensed and the residues are chromatographically refined with a chloroform/methanol mixture having a proportion of 10/1, so that 21.3 g of Compound 79 can be obtained.

Melting point: 79.5° to 81.0° C.

M+-1 = 342 is detected with FAB-MS.

Exemplified compound 82 can be synthesized in the following method.

Exemplified compound 82 can be obtained in the same reaction as in the above-mentioned synthesis of Compound 79, except that 1-methyl-1-phenylhydrazine is replaced by 1,1-dimethylhydrazine and, in addition, an autoclave is used.

Melting point: 158° to 159° C.

M+ = 281 is detected with FAB-MS.

Exemplified compound 83 can be synthesized in the following method.

Exemplified compound 83 can be obtained in the same reaction as in the above-mentioned synthesis of Compound 79, except that 1-methyl-1-phenylhydrazine is replaced by 1,1-diphenylhydrazine.

Melting point: 230° to 231° C.

M+ = 405 is detected with FAB-MS.

Exemplified Compound 85 can be synthesized in the following method.

Compound 85 can be obtained in the same reaction as in the above-mentioned synthesis of Compound 79, except that 1-methyl-1-phenylhydrazine is replaced by phenylhydrazine.

Melting point : 194° to 195° C.
M+ =329 is detected with FAB-MS.

The methods of synthesizing the compounds relating to the invention may also be referred to those methods described in Japanese Patent O.P.I. Publication No. 55-52050/1980, U.S. Pat. No. 4,686,167 and so forth.

Silver halide photographic light-sensitive materials of the invention each contain the compounds represented by the foregoing Formula I. In such silver halide photographic light-sensitive materials of the invention, the compounds represented by the foregoing Formula I should be contained in an amount of, preferably, from $5 \times 10^{31\ 7}$ mols to $5 \times 10^{-1}$ mols per mol of silver halides contained in such silver halide photographic light-sensitive materials of the invention and, more preferably, within the range of from $5 \times 10^{-5}$ mols to $1 \times 10^{-2}$ mols, in particular.

Silver halide photographic light-sensitive materials of the invention each comprise at least one silver halide emulsion layer. To be more concrete, there may be some instance where at least one silver halide emulsion layer may be provided to one side of a support, or there may be another instance where at least one layer is provided to each of the both sides of the support. Silver halide emulsion may be coated over a support either directly or through the other layer such as a hydrophilic colloidal layer not containing any silver halide emulsion. In addition, a hydrophilic colloidal layer may also be coated as a protective layer over a silver halide emulsion layer. Such silver halide emulsion layer may also be provided so as to be separated into some silver halide emulsion layers each having a different sensitivity such as a high-speed silver halide emulsion layer and a lowe-speed one. In this case, it is allowed to interpose an interlayer comprising hydrophilic colloids either between the silver halide emulsion layers or between a silver halide emulsion layer and a protective layer. In other words, it is allowed to provide non-light-sensitive hydrophilic colloidal layers such as an interlayer, a protective layer, an antihalation layer, a backing layer and so forth, if required.

When adding a compound represented by Formula I into a silver halide photographic light-sensitive material of the invention, it is preferable to add the compound into a hydrophilic colloidal layer of the light-sensitive material and it is particularly preferable to add it into a silver halide emulsion layer and/or a hydrophilic colloidal layer adjacent to the above-mentioned silver halide emulsion layer.

No matter what is preferable, it is nevertheless allowed to add it into any other layer than silver halide emulsion layers. For example, it is allowed as a matter of course to add it into any other hydrophilic colloidal layer laminated on the above-mentioned emulsion layer.

In the most preferable embodiment of the invention, a compound represented by Formula I is added into a silver halide emulsion layer and a hydrophilic colloid is comprised of gelatin or a gelatin derivative.

Next, how to add a compound represented by Formula I into a hydrophilic colloidal layer will be detailed. These methods include, for example, a method of adding the compound upon dissolving the compound in water and/or a suitable organic solvent, another method of adding it in such a manner that a solution prepared by dissolving the compound and an organic solvent together is dispersed into a hydrophilic colloid matrix of gelatin, gelatin derivatives or the like, a further method of adding it upon dispersing it into a latex, and so forth. Any of these methods may be used when embodying the invention. When adding the compounds represented by Formula I, preferable image characteristics may be obtained even if adding one kind of the compounds independently and, on the other hand, it has been confirmed to allow them to be used in combination in a suitable proportion.

Besides the above-given methods, it is also allowed to use another method of adding the compounds represented by Formula I, in which the compounds are dissolved in a suitable solvent including, for example, water, alcohols such as methanol, ethanol or the like, ethers, esters, and so forth, and the resulting solution is coated directly, in an over-coating method or the like, over the portion serving as the outermost layer of the silver halide emulsion layers of a silver halide photographic light sensitive material so that the compounds may be added in the light-sensitive material.

As described above, the preferable embodiments of the invention include, for example, an embodiment in which the compounds represented by Formula I are added into a silver halide emulsion layer, and another embodiment in which the compounds represented by Formula I are added into a hydrophilic colloidal layer adjacent to the other hydrophilic colloidal layer either directly or through an interlayer.

Next, the silver halides applicable to the silver halide photographic light-sensitive materials of the invention will now be detailed. Silver halides having any composition may be used. Those silver halides include, for example, silver chloride, silver chlorobromide, silver chloroiodobromide, pure silver bromide or pure silver chloroiodobromide. An average grain size of the above-mentioned silver halide grains should be within the range of, preferably, from 0.05 to 0.5 µm and, more preferably, from 0.10 to 0.40 µm.

Any grain distribution of the silver halide grains applicable to the invention may be used. These distribution is so adjusted as to be within the range of, preferably, from 1 to 30 in terms of monodispersion degree which is defined below and, more preferably, from 1 to 20.

The above-mentioned monodispersion degree is defined as follows.

$$\text{Monodispersion degree} = \sqrt{\frac{\Sigma (r - ri)^2 ni}{\Sigma ni}} \div r \times 100$$

Here, ri represents grain size of the respective grains, and ni, the number thereof. The average grain size $\bar{r}$ indicates the length of a side in the case of a cubic silver halide grain, and, in the case of a spherical one, an average value of the length of a side when converted into a cube. When the grain size of the respective grains is ri and the number thereof is ni, the above formulas can be applied.

A monodispersion degree is defined as a numerical value obtained by centupling a quotient of a standard deviation of grain sizes as a dividend and an average grain size as a divisor.

Silver halide grains which are used for embodying the invention include, for example, those having at least two or more layered structure. To be more concrete, it is allowed to use silver chlorobromide grains comprising a combination of silver chloride core and a silver bromide shell, and vice versa. In this case, iodides may be added into any layers and, more preferably, they are added in an amount of not more than 5 mol%.

Further, when preparing a silver halide emulsion, sensitivity or contrast can be controlled by adding a rhodium salt. In general, it is preferable to add the above-mentioned rhodium salts at the point of time when silver halide grains are formed. It is, however, allowed to add them when chemically ripening or when preparing an emulsion coating liquid. Such rhodium salts may be not only a simple salt but also a double salt. Typically applicable ones include, for example, rhodium trichloride, rhodium ammonium chloride and so forth.

Rhodium salts may be added in any amount to satisfy desired sensitivity and contrast and, more effectively, in an amount within the range of $10^{-9}$ to $10^{-4}$ moles per mol of silver.

When using such rhodium salts, it is also allowed to use other inorganic compounds such as an iridium salt, a platinum salt, a thallium salt, a cobalt salt, a gold salt and so forth. In particular, iridium salts are often used for providing an emulsion improved in characteristics for high intensity exposure In this case, they are preferably used in an amount within the range of $10^{-9}$ to $10^{-4}$ mols per mol of silver.

Further, silver halides can be sensitized with a variety of chemical sensitizers including, for example, active gelatin: sulfur sensitizers such as sodium thiosulfate, allyl thiocarbamide, thiourea, allylisothiacyanate and so forth; selenium sensitizers such as N,N-dimethyl-selenourea, selenourea and so forth; reduction sensitizers such as triethylenetetramine, stannous chloride and so forth: various noble metal sensitizers including typically potassium chloroaurite, potassium aurithiocyanate, potassium chloroaurate, 2-aurosulfobenzothiazolemethylchloride, ammonium chloropalladate, potassium chloroplatinate and sodium chloropalladite; and so forth. These sensitizers may be use independently or in combination. Further, when using a gold sensitizer, ammonium thiocyanate may also be used as an assistant.

The invention is suitably used when an emulsion contains surface latent image type grains as silver halide grains. Such surface latent image type grains mean those prepared so as to make sensitivity higher in processing with a developer called a surface developer in photographic industry than in processing with an internal developer.

Silver halide emulsions applicable to the invention can be stabilized or fog-prevented with mercapto compounds such as 1-phenyl-5-mercaptotetrazole and 2-mercaptobenzthiazole, benzotriazole compounds such as 5-brombenzotriazole and 5-methylbenzotriazole, benzimidazole compounds such as 6-nitrobenzimidazole, and the like compounds.

Silver halide emulsions applicable to the invention can be added with sensitizing dyes, plasticizers, antistatic agents, surfactants, hardeners and so forth.

When adding the compounds relating to the invention represented by Formula I into a hydrophilic colloidal layer, gelatin is suitable for the binder of the hydrophilic colloidal layer and it is, however, allowed to use other hydrophilic colloids than gelatin, for the binder.

Supports applicable to the embodiments of the invention include, for example, baryta paper, polyethylene-coated paper, polypropylene synthetic paper, glass plate, cellulose acetate film, cellulose nitrate film or polyester films such as polyethyleneterephthalate film, and so forth. These supports may be suitably selected to meet the purposes of silver halide photographic light-sensitive materials.

For the purpose of developing the silver halide photographic light-sensitive materials of the invention, the following developing agents can be used. These developing agents include, typically, HO—(CH=CH-)n—OH type developing agents such as hydroquinone and, besides the above, catechol, pyrogallol and so forth.

Further, HO—(CH=CH)n—NH$_2$ type developing agents include typically, ortho- and para-aminophenols or aminopyrazolones such as N-methyl-p-aminophenol, N-$\beta$-hydroxyethyl-p-aminophenol, p-hydroxyphenylaminoacetic acid, 2-aminonaphthol and so forth.

Heterocyclic type developing agents include, for example, 3-pyrazolidones such as 1-phenyl-3-pyrazolidone, 1-phenyl-4,4-dimethyl-3-pyrazolidone, 1-phenyl-4-methyl-4-hydroxymethyl-3-pyrazolidone, and so forth.

Besides the above, the developing agents effectively applicable to the invention include, for example, those described in T. H. James, The Theory of the Photographic Process, 4th Edition, pp. 291–334 and Journal of the American Chemical Society Vol. 73. p. 3,100, 1951.

These developing agents can be used independently or in combination. It is, however, preferable to use them in combination. It is preferable to use hydroquinone if using them inedpendently, and a combination of hydroquinone and either 1-phenyl-3-pyrazolidone or N-methyl-p-aminophenol if using them in combination.

The effects of the invention cannot be damaged even if preservatives including sulfites such as sodium sulfite, potassium sulfite and so forth should be added into a developer applicable to the processes of developing the light-sensitive materials of the invention. Hydroxylamine or hydrozide compounds may also be used as such a preservative. It is also allowed to use additives including, for example, pH adjusting agents or buffers such as caustic alkali, alkaline carbonate, amine and so forth which may be used in general type black-and-white developers, inorganic development inhibitors such as potassium bromide and so forth, organic development inhibitors such as benzotriazole and so forth, sequestering agents such as ethylenediaminetetraacetic acid and so forth, development accelerators such as methanol, ethanol, benzyl alcohol, polyalkylene oxide and so forth, surfactants such as sodium alkylarylsulfonate, natural saponin, sugar or the alkyl esters of the foregoing compounds and so forth, hardeners such as glutaraldehyde, formalin, glyoxal and so forth, ionic strength adjusting agent such as sodium sulfate and so forth.

Developers applicable to the invention are allowed to contain alkanolamines or glycols, as an organic solvent.

EXAMPLE

Examples of the invention will now be detailed below. It is, however, a matter of course that the invention shall not be limited only to the following examples.

EXAMPLE-1

The samples were prepared each by adding an exemplified compound represented by Formula I and a comparative compound shown in Table-1 into a silver halide emulsion layer of photographic light-sensitive material.

Preparation of Silver Halide Photographic Light-Sensitive Materials

Sample Nos. 1 through No. 23 of silver halide photographic light-sensitive material were prepared in the following manner.

On both sides of a 100 μm-thick polyethyleneterephthalate film, 0.1 μm-thick subbing layers were coated, respectively. On the subbing layer coated on one side of the film, a silver halide emulsion having the following composition (1) was coated so that the gelatin and silver contents were to be 1.5 g/m² and 3.3 g/m², respectively.

On the silver halide emulsion layer, a protective layer having the following composition (2) was further coated so that the gelatin content was to be 1.0 g/m². On the other subbing coat layer coated on the opposite side of the film, a backing layer having the following composition (3) was coated so that the gelatin content was to be 3.5 g/m². On the backing layer, another protective layer having the following composition (4) was coated so that the gelatin content was to be 1 g/m². Thus Samples Nos. 1 through 23 was prepared.

Composition (1) of the silver halide emulsion layer

| | |
|---|---|
| Gelatin | 1.5 g/m² |
| Silver chlorobromide grains containing AgCl of 60 mol % and AgBr of 40 mol %, having a monodispersion degree of 12, and containing rhodium and iridium each of $10^{-6}$ mol mol per mol of Ag | 3.3 g/m² |
| Antifoggant: 4-hydroxy-6-methyl-1,3,3a,7-tetrazaindene | 0.30 g/m² |
| Compound represented by Formula I or a comparative compound For the amount added, refer to Table 1 | |
| Surfactant: saponin | 0.1 g/m² |
| Latex polymer: polyethyl acrylate - acrylic acid copolymer | 1 g/m² |
| Sensitizing dye: Four kinds of those having the following chemical structures (A) through (D) were used in combination. | |

(A) Regular sensitizing dye

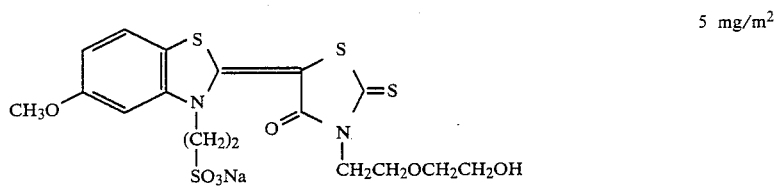

5 mg/m²

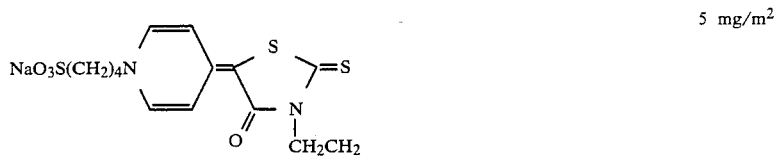

5 mg/m²

(B) Ortho sensitizing dye

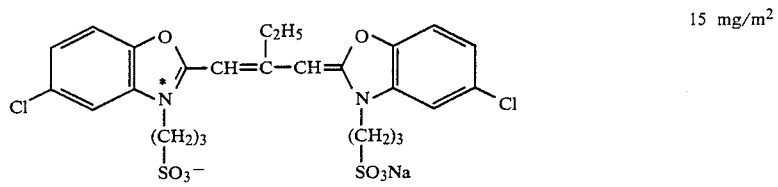

15 mg/m²

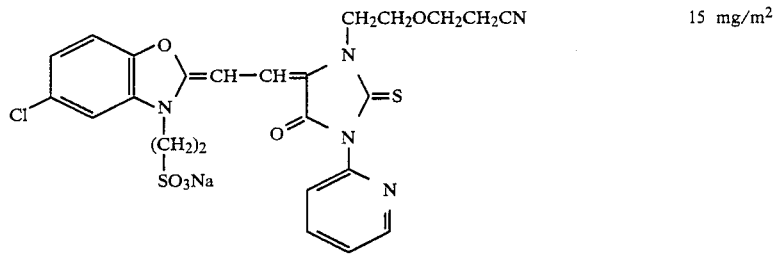

15 mg/m²

(C) Panchromatic sensitizing dye

-continued

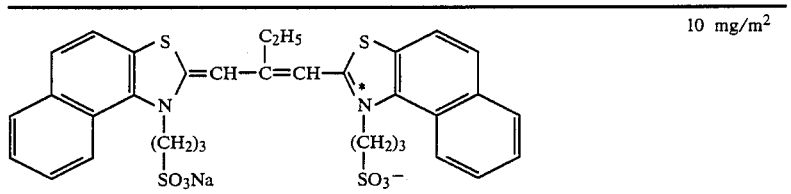
10 mg/m²

(D) Infrared sensitizing dye

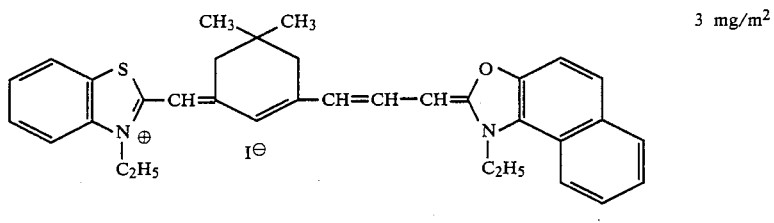
3 mg/m²

Development controlling agents:

| | |
|---|---|
| Nonylphenoxypolyethylene glycol | 10 mg/m² |
| 5-methylbenzotriazole | 7 mg/m² |
| Adenine | 3 mg/m² |
| Guanine | 2 mg/m² |
| Uracil | 2 mg/m² |
| Adenosine | 2 mg/m² |
| 1-phenyl-5-mercaptotetrazole | 3 mg/m² |
| Hydroquinone | 100 mg/m² |
| Phenidone | 10 mg/m² |
| Butyl gallate | 40 mg/m² |
| Promethazine hydrochloride | 43 mg/m² |
| Thiaramido hydrochloride | 36 mg/m² |
| n-butyldiethanolamine | 10 mg/m² |

Composition (2) of the emulsion protective layer

| | |
|---|---|
| Gelatin | 1.0 g/m² |
| Matting agent: polymethyl methacrylate having an average particle size of 3.0 to 5.0 μm | 0.05 g/m² |
| Surfactant: sodium n-dodecylbenzenesulfonate | 0.01 g/m² |
| Antistatic agent: $C_8F_{17}COONH_4$ | 10 mg/m² |
| NaCl | 100 mg/m² |
| LiCl | 30 mg/m² |
| ITO* | 30 mg/m² |
| Stabilizer: 1-phenyl-5-mercaptotetrazole | 3 mg/m² |

5 mg/m²

Hardener: Formalin     0.03 g/m²

*ITO: A antistatic agent comprising a mixture of indium oxide and tin oxide, which contains indium of not less than 95%.

Composition (3) of backing layer

| | |
|---|---|
| Gelatin | 3.5 g/m² |
| Dye: | |

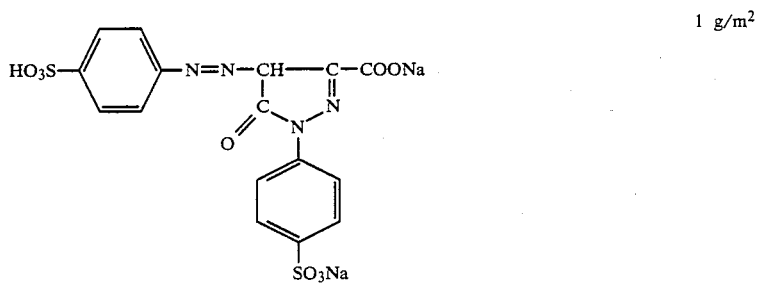
1 g/m²

-continued

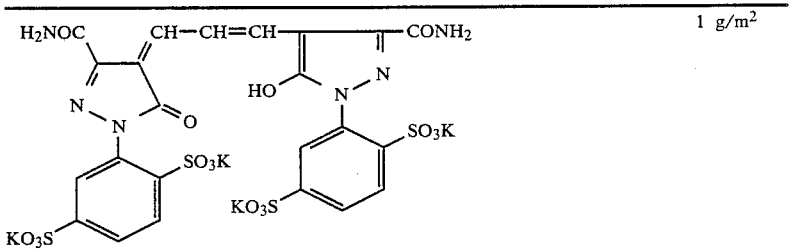 1 g/m²

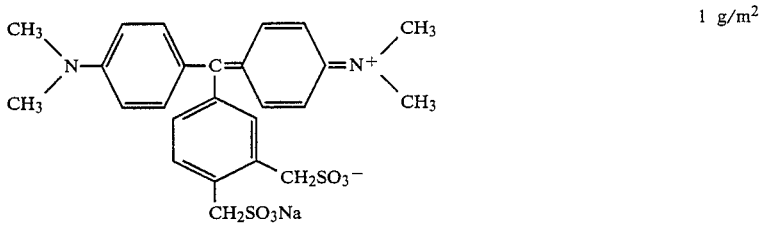 1 g/m²

| | |
|---|---|
| Surfactant: saponin | 0.1 g/m² |
| Hardener: Glyoxal | 0.1 g/m² |

 0.1 g/m²

Composition (4) of backing protective layer

| | |
|---|---|
| Gelatin | 1 g/m² |
| Matting agent: polymethyl methacrylate having an average particle size of 3.0 to 5. μm | 0.5 g/m² |
| Surfactant: sodium p-dodecylbenzenesulfonate | 0.01 g/m² |

$C_8F_{17}SO_2NH(CH_2)_3\overset{+}{N}(CH_3)_2—CH_2COO^-$     0.01 g/m²

| | | |
|---|---|---|
| Development controlling agent: | 5-nitroindazole | 0.012 g/m² |
| | 5-methylbenzotriazole | 0.02 g/m² |
| | 1-phenyl-5-mercaptotetrazole | 0.005 g/m² |

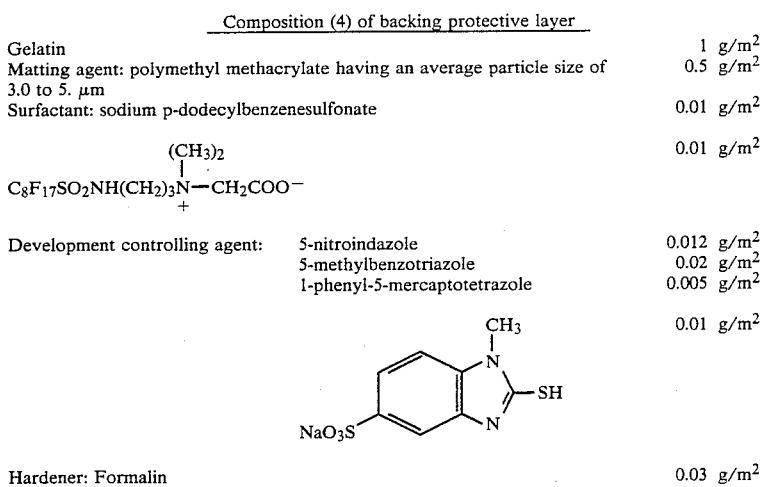 0.01 g/m²

| | |
|---|---|
| Hardener: Formalin | 0.03 g/m² |

The samples prepared were subject to halftone dot quality tests in the following procedures.

Halftone Dot Quality Test Procedures

A sample was brought into close contact with a step wedge partly attached with a 50% halftone hard dot contact screen with 150 lines per inch, and the sample was exposed to a xenon light source for 5 seconds. Under the following conditions, the exposed sample was developed with a rapid processing type automatic processor into which the following developer and fixer were used. The halftone dot quality of the sample was inspected with a 100× magnifier. The inspected halftone dot qualities were graded by 5 ranks from 5 points to 1 point in order from 'excellent' to 'poor'. The ranks of 1 and 2 points were on a quality level unfavorable for putting them to practical use.

Fog produced in halftone dots were similarly evaluated and graded by 5 ranks from 5 points to 1 point in order from the highest without having no black spot or pepper spot at all to the lowest. The ranks of 1 and 2 points were on a quality level unfavorable for putting them to practical use, because they had large black spots.

| Developer | |
|---|---|
| Composition A | |
| Pure water, i.e., ion-exchanged water | 150 ml |
| Disodium ethylenediaminetetraacetate | 2 g |
| Diethylene glycol | 50 g |
| Phosphoric acid | 10 g |
| Potassium sulfite in an aqueous 55% w/v solution | 100 ml |
| Potassium carbonate | 50 g |
| Hydroquinone | 15 g |
| 5-methylbenzotriazole | 200 mg |
| 1-phenyl-5-mercaptotetrazole | 30 mg |
| Potassium hydroxide | 11.5 |
| An amount to make pH of the solution be pH | |
| Potassium bromide | 3 g |

| Developer | |
|---|---|
| Composition B | |
| Pure water, i.e., ion-exchanged water | 3 ml |
| Diethylene glycol | 50 g |
| 3-diethylamino-1,2-propanediol | 15 g |
| Disodium ethylenediaminetetraacetate | 25 mg |
| Acetic acid, in an aqueous 90% solution | 0.3 ml |
| 5-nitroindazole | 110 mg |
| Sodium 2-mercaptobenzimidazole-5-sulfonate | 30 mg |
| 1-phenyl-3-pyrazolidone | 500 mg |
| N-methyl-p-aminophenol | 2.5 mg |

When using a developer, the above-given composition A and B were dissolved in order in 500 ml of water to make one liter, and the developer was used.

| Fixer | |
|---|---|
| Composition A | |
| Ammonium thiosulfate, in an aqueous 72.5% w/v solution | 240 ml |
| Sodium sulfite | 17 g |
| Sodium acetate trihydrate | 6.5 g |
| Boric acid | 6 g |
| Sodium citrate, dihydrate | 2 g |
| Acetic acid, in an aqueous 90% w/v solution | 13.6 ml |
| Composition B | |
| Pure water, i.e., ion-exchanged water | 17 ml |
| Sulfuric acid, in an aqueous 50% w/v solution | 4.7 g |
| Aluminium sulfate, an aqueous solution having an equivalent $Al_2O_3$ content of 8.1% w/v | 26.5 g |

When using a fixer, the above-given compositions A and B were dissolved in order in 500 ml of water to make one liter and the fixer was used. pH of the fixer was about pH4.3.

| | Development conditions | |
|---|---|---|
| Step | Temperature | Time |
| Developing | 38° C. | 30 sec. |
| Fixing | 28° C. | 20 sec. |
| Washing | Ordinary temperature | 20 sec. |

The following comparative compounds (a) through (e) were added to the silver halide emulsion layer having the composition (1).

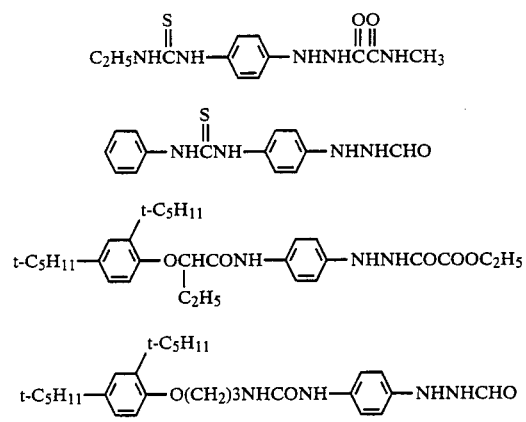

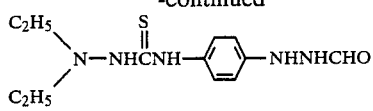

Test Results

With respect to the samples of the invention No. 1 through No. 33 and samples No. 34 through No. 38 prepared by making use of the above-given comparative compounds (a), (b), (c), (d) and (e), Table-1 shows the compounds and their amounts added to the silver halide emulsion layers of these samples. In Table-1, the compounds represented by Formula I are indicated by the aforegiven exemplified compound numbers.

Table-2 shows the results of the halftone dot quality tests of the samples with their quality ranks.

As is obvious from Table-2, in the halftone dot quality evaluation, the samples relating to the invention No. 1 through No. 33 resulted all in not lower than 4 point-rank and the 5 point-ranked samples were more than the 4 point-ranked. The comparative samples No. 34 through No. 38 resulted all in 3 point-rank. Judging that 1 point-rank and 2 point-rank are on a level unfavorable for practical use, it was proved that the halftone dot qualities of samples No. 34 through No. 38 can hardly be good, but those of samples relating to the invention No. 1 through No. 33 can be high and excellent.

With respect to the black spot production degree that serves as a fog indicator, it was proved that the samples relating to the invention No. 1 through NO. 33 were evaluated to be 5 or 4 point-rank and showed the very good results without any fog, while the comparative examples No. 34 through No. 38 were evaluated to be not higher than 2 point-rank and showed the results hardly acceptable to practical use.

TABLE 1

| Sample No. | Compound | Amount added per mol of Ag | Note |
|---|---|---|---|
| 1 | (1) | $5 \times 10^{-4}$ mol | Invention |
| 2 | (2) | $5 \times 10^{-4}$ mol | Invention |
| 3 | (3) | $5 \times 10^{-4}$ mol | Invention |
| 4 | (4) | $5 \times 10^{-4}$ mol | Invention |
| 5 | (5) | $5 \times 10^{-4}$ mol | Invention |
| 6 | (10) | $5 \times 10^{-4}$ mol | Invention |
| 7 | (14) | $5 \times 10^{-4}$ mol | Invention |
| 8 | (15) | $5 \times 10^{-4}$ mol | Invention |
| 9 | (17) | $5 \times 10^{-4}$ mol | Invention |
| 10 | (18) | $5 \times 10^{-4}$ mol | Invention |
| 11 | (23) | $5 \times 10^{-4}$ mol | Invention |
| 12 | (26) | $5 \times 10^{-4}$ mol | Invention |
| 13 | (33) | $5 \times 10^{-4}$ mol | Invention |
| 14 | (35) | $5 \times 10^{-4}$ mol | Invention |
| 15 | (36) | $5 \times 10^{-4}$ mol | Invention |
| 16 | (39) | $5 \times 10^{-4}$ mol | Invention |
| 17 | (44) | $5 \times 10^{-4}$ mol | Invention |
| 18 | (50) | $5 \times 10^{-4}$ mol | Invention |
| 19 | (52) | $5 \times 10^{-4}$ mol | Invention |
| 20 | (60) | $5 \times 10^{-4}$ mol | Invention |
| 21 | (79) | $5 \times 10^{-4}$ mol | Invention |
| 22 | (80) | $5 \times 10^{-4}$ mol | Invention |
| 23 | (82) | $5 \times 10^{-4}$ mol | Invention |
| 24 | (83) | $5 \times 10^{-4}$ mol | Invention |
| 25 | (84) | $5 \times 10^{-4}$ mol | Invention |
| 26 | (86) | $5 \times 10^{-4}$ mol | Invention |
| 27 | (87) | $5 \times 10^{-4}$ mol | Invention |
| 28 | (88) | $5 \times 10^{-4}$ mol | Invention |
| 29 | (89) | $5 \times 10^{-4}$ mol | Invention |
| 30 | (90) | $5 \times 10^{-4}$ mol | Invention |
| 31 | (92) | $5 \times 10^{-4}$ mol | Invention |
| 32 | (93) | $5 \times 10^{-4}$ mol | Invention |
| 33 | (96) | $5 \times 10^{-4}$ mol | Invention |

TABLE 1-continued

| Sample No. | Compound | Amount added per mol of Ag | Note |
|---|---|---|---|
| 34 | a | $5 \times 10^{-4}$ mol | Comparison |
| 35 | b | $5 \times 10^{-4}$ mol | Comparison |
| 36 | c | $5 \times 10^{-4}$ mol | Comparison |
| 37 | d | $5 \times 10^{-4}$ mol | Comparison |
| 38 | e | $5 \times 10^{-4}$ mol | Comparison |

TABLE 2

| Sample No. | Halftone dot quality | Black spot | Note |
|---|---|---|---|
| 1 | 5 | 5 | Invention |
| 2 | 5 | 5 | Invention |
| 3 | 4 | 5 | Invention |
| 4 | 4 | 4 | Invention |
| 5 | 4 | 5 | Invention |
| 6 | 5 | 5 | Invention |
| 7 | 4 | 5 | Invention |
| 8 | 5 | 4 | Invention |
| 9 | 5 | 5 | Invention |
| 10 | 4 | 5 | Invention |
| 11 | 5 | 4 | Invention |
| 12 | 5 | 5 | Invention |
| 13 | 5 | 4 | Invention |
| 14 | 5 | 5 | Invention |
| 15 | 5 | 5 | Invention |
| 16 | 4 | 4 | Invention |
| 17 | 5 | 5 | Invention |
| 18 | 4 | 4 | Invention |
| 19 | 5 | 5 | Invention |
| 20 | 5 | 5 | Invention |
| 21 | 5 | 5 | Invention |
| 22 | 5 | 5 | Invention |
| 23 | 5 | 5 | Invention |
| 24 | 5 | 5 | Invention |
| 25 | 5 | 5 | Invention |
| 26 | 5 | 5 | Invention |
| 27 | 5 | 5 | Invention |
| 28 | 5 | 5 | Invention |
| 29 | 5 | 5 | Invention |
| 30 | 5 | 5 | Invention |
| 31 | 5 | 5 | Invention |
| 32 | 5 | 5 | Invention |
| 33 | 5 | 5 | Invention |
| 34 | 3 | 2 | Comparison |
| 35 | 3 | 2 | Comparison |
| 36 | 3 | 1 | Comparison |
| 37 | 3 | 2 | Comparison |
| 38 | 3 | 1 | Comparison |

EXAMPLE-2

Samples No. 39 through No. 58 were prepared in the same manner as in Samples No. 1, No. 14, No. 21 and No. 25 of Example-1, except that the monodispersion degrees, i.e., the uniformity in grain size, of silver halide grains were changed to 4 to 40, and were then tested.

When preparing the grains, rhodium and iridium were added thereto in the amounts of $8 \times 10^{-7}$ mol and $3 \times 10^{-7}$ mol each per mol of Ag, respectively. The silver halide composition of this example was that of silver chlorobromide grains containing silver chloride of 98 mol%. Further, the desensitizing dye having the following structure was added in place of sensitizing dyes (A), (B), (C) and (D).

Desensitizing dye in which the sum of anodic potential and cathodic potential each of a polarograph was positive.

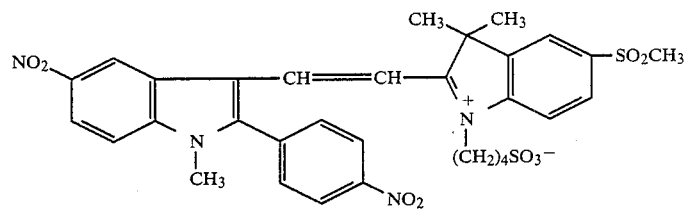

Further, 50 mg/m² of the following filter dye were added into a protective layer.

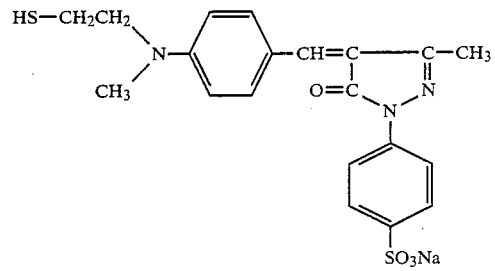

Maximum absorption wavelength (H₂O)
max: 492 nm

Also, 100 mg/m² of the following UV-absorbing dye were added.

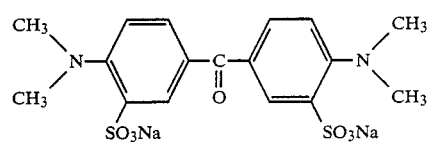

The other preparation procedures than the above were carried out in the same manner as in the foregoing samples Nos. 1, 14, 21 and 25, for example, the same exemplified compounds Nos. 1, 35, 70 and 84 were used as the compounds represented by Formula I. Monodispersion degrees can be adjusted in an ordinary controlled double-jet precipitation method in such a manner that a pH potential and the supplying amounts of Ag+ and halide ions are suitably changed, when grains are prepared.

Exposures and developments were also carried out in almost the same manner as in Example-1, and the photographic characteristics were evaluated, provided that, in this example, the prepared samples were exposed to an extra-high pressure mercury lamp with an energy of 5mJ.

The results of the evaluation are shown in Table-3 from which it was proved that Samples No. 32 through No. 58 each were excellent in halftone dot quality ranked as 4.5 to 5 points and less in black spot production ranked as 4.5 to 5 points, that is, they had a high halftone dot quality and very few fog.

TABLE 3

| Sample No. | Compound | Monodispersion degree of silver halide grains | Photographic characteristics | |
|---|---|---|---|---|
| | | | Halftone dot quality | Black spot production |
| 39 | 1 | 40 | 4.5 | 4.5 |
| 40 | 1 | 35 | 4.6 | 4.7 |
| 41 | 1 | 20 | 4.8 | 4.8 |
| 42 | 1 | 10 | 5 | 5 |
| 43 | 1 | 4 | 5 | 5 |
| 44 | 35 | 40 | 4.5 | 4.5 |
| 45 | 35 | 35 | 4.7 | 4.6 |
| 46 | 35 | 20 | 4.8 | 4.7 |
| 47 | 35 | 10 | 5 | 5 |
| 48 | 35 | 4 | 5 | 5 |
| 49 | 79 | 40 | 4.6 | 4.6 |
| 50 | 79 | 35 | 4.7 | 4.8 |
| 51 | 79 | 20 | 4.9 | 4.9 |
| 52 | 79 | 10 | 5 | 5 |
| 53 | 79 | 4 | 5 | 5 |
| 54 | 84 | 40 | 4.6 | 4.6 |
| 55 | 84 | 35 | 4.8 | 4.7 |
| 56 | 84 | 20 | 4.9 | 4.9 |
| 57 | 84 | 10 | 5 | 5 |
| 58 | 84 | 4 | 5 | 5 |

What is claimed si:

1. A light-sensitive silver halide photographic material comprising at least one silver halide emulsion layer containing surface latent image type silver halide grains and a compound represented by the following formula I;

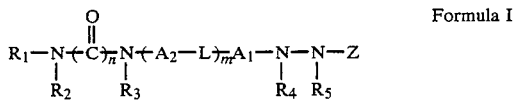

Formula I wherein $A_1$ and $A_2$ are each an arylene group or a heterocyclic group; L is a bonding group; Z is a formyl group, and acyl group, an alkoxycarbonyl group, a thioacyl group or a

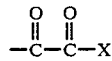

group; X is $-NR_6R_7$ or $-OR_8$, in which $R_6$ and $R_7$ are each a hydrogen atom, an alkyl group, an alkenyl group, an alkynyl group, an aryl group, a heterocyclic group, a hydroxy group, an alkoxy group, an alkenylkoxy group, an alkynyloxy group, an aryloxy group or a heterocyclic oxy group, the groups represented by $R_6$ and $R_7$ may be bonded together to form a ring, and $R_8$ is a hydrogen atom, an alkyl group, an alkenyl group, an alkynyl group, an aryl group or a heterocyclic group; n is 1 or 2; m is 0 or 1; and $R_1$ and $R_2$ are each a hydrogen atom, an alkyl group, an alkenyl group, an aryl group, a heterocyclic group or an amino group; $R_3$ is a hydrogen atom or an alkyl group; each pair of $R_1$ and $R_2$, and $R_1$ and $R_3$ may be bonded together to form a ring, provided that when n is 1, at least one of the $R_1$ and $R_2$ is an amino group; and $R_4$ and $R_5$ are each a hydrogen atom or a substituent.

2. The material of claim 1, wherein n is 1, and at least one of the $R_1$ and $R_2$ is an

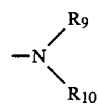

group, in which $R_8$ and $R_{10}$ are each an alkyl group, a alkenyl group, an alkynyl group, an aryl group or a heterocyclic group, provided that the $R_9$ and $R_{10}$ may be bond together to form a ring.

3. The material of claim 1, wherein said $R_4$ and $R_5$ are each a hydrogen atom, a sulfonyl group, an acyl group or an oxalyl group.

4. The material of claim 1, wherein said group represented by Z is a formyl group, an acyl group or a

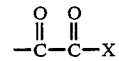

group.

5. The material of claim 1, wherein said compound represented by formula I has an anti-diffusion group 6. The material of claim 5, wherein said anti-diffusion group has at least eight carbon atoms and is an alkyl group, an alkoxy group, a phenyl group, an alkylphenyl group, a phenoxy group or an alkylphenoxy group.

7. The material of claim 1, wherein said compound represented by formula I has a group accelerating adsorption to silver halide.

8. The material of claim 7, wherein said accelerating adsorption to silver halide is a thiourea group, a thiourethane group, a heterocyclic thioamido group a mercaptoheterocyclic group or a triazole group.

9. The material of claim 1, wherein said compound represented by formula I is contained in an amount of from $5 \times 10^{-7}$ mol to $5 \times 10^{-1}$ mol per mol of silver halide contained in said light sensitive material.

10. The material of claim 9, wherein said compound represented by formula I is contained in an amount of from $5 \times 10^{-5}$ mol to $1 \times 10^{-2}$ mol per mol of silver halide contained in said light-sensitive.

11. The material of claim 1, wherein said compound represented by formula I is contained in said silver halide emulsion layer.

12. The material of claim 1, wherein said compound represented by formula I is contained in a hydrophilic colloid layer included in said silver halide photographic light-sensitive material.

13. The material of claim 1, wherein said compound represented by formula I is contained in at least one of said silver halide emulsion layer and a hydrophilic colloid layer adjacent to said silver halide emulsion layer.

14. The material of claim 1, wherein silver halide grains contained said silver halide emulsion layer have a monodispersion degree of from 1 to than 30.

15. The material of claim 14, wherein said silver halide grains have a monodispersion degree of from 1 to than 20.

* * * * *

UNITED STATES PATENT AND TRADEMARK OFFICE
CERTIFICATE OF CORRECTION

PATENT NO. : 4,977,063

DATED : December 11, 1990

INVENTOR(S) : Yasushi Usagawa et al.

It is certified that error appears in the above-identified patent and that said Letters Patent is hereby corrected as shown below:

Claim 1, Column 45, Line 25, "si" should be --is--;

Claim 2, Column 46, Line 9, "$R_8$" should be --$R_9$--;

Claim 2, Column 46, Line 9, "a" should be --an--;

Claim 2, Column 46, Line 12, "be bond" should be --be bonded;

Claim 5, Column 46, Line 25, "group" should be followed by --.--;

Claim 8, Column 46, Line 35, "thioamido group" should be followed by --,--.

UNITED STATES PATENT AND TRADEMARK OFFICE
CERTIFICATE OF CORRECTION

PATENT NO. : 4,977,063

DATED : December 11, 1990

INVENTOR(S) : Yasushi Usagawa et al

It is certified that error appears in the above-identified patent and that said Letters Patent is hereby corrected as shown below:

Claim 10, Column 46, Line 44, "light-sensitive" should be followed by --material--.

Signed and Sealed this

Twentieth Day of October, 1992

Attest:

DOUGLAS B. COMER

Attesting Officer

Acting Commissioner of Patents and Trademarks